United States Patent
Kanodia et al.

(10) Patent No.: US 7,153,317 B2
(45) Date of Patent: Dec. 26, 2006

(54) DISPOSABLE GUARDED SURGICAL SCALPEL

(75) Inventors: Rajender K. Kanodia, New Delhi (IN); Ilija Djordjevic, East Granby, CT (US); Sushil K. Kanwar, New Britain, CT (US); Vikram Kanodia, New Delhi (IN); Avinash Kanodia, New Delhi (IN); Deepak Jain, New Delhi (IN)

(73) Assignee: Ribbel International Limited, New Delhi (IN)

( * ) Notice: Subject to any disclaimer, the term of this patent is extended or adjusted under 35 U.S.C. 154(b) by 90 days.

(21) Appl. No.: 10/452,415

(22) Filed: May 30, 2003

(65) Prior Publication Data

US 2004/0243161 A1 Dec. 2, 2004

(51) Int. Cl.
*A61B 17/32* (2006.01)

(52) U.S. Cl. ............................ 606/167; 30/162; 30/335

(58) Field of Classification Search ................ 606/167, 606/172; 30/162
See application file for complete search history.

(56) References Cited

U.S. PATENT DOCUMENTS

| | | | | |
|---|---|---|---|---|
| 5,071,426 A | * | 12/1991 | Dolgin et al. ............... | 606/167 |
| 5,250,063 A | * | 10/1993 | Abidin et al. ............... | 606/167 |
| 5,330,494 A | * | 7/1994 | van der Westhuizen et al. . | 606/167 |
| 5,411,512 A | * | 5/1995 | Abidin et al. ............... | 606/167 |
| 5,417,704 A | * | 5/1995 | Wonderley ................... | 606/167 |
| 5,527,329 A | * | 6/1996 | Gharibian .................... | 606/167 |
| 5,620,454 A | * | 4/1997 | Pierce et al. ................. | 606/167 |
| 5,683,407 A | * | 11/1997 | Jolly et al. ................... | 606/181 |
| 5,938,676 A | * | 8/1999 | Cohn et al. .................. | 606/167 |

* cited by examiner

*Primary Examiner*—Corrine McDermott
*Assistant Examiner*—Christopher Prone
(74) *Attorney, Agent, or Firm*—Alix, Yale & Ristas, LLP

(57) ABSTRACT

A disposable guarded surgical scalpel includes a handle with a blade fixed to it and a slidably mounted guard. The guard can be moved using a single hand. When the scalpel is in use the guard is moved to a retracted position where the blade is exposed; the guard locks in this position to prevent any unintentional movement. When the scalpel is not in use, the guard is moved to an extended position where the blade is covered. When the scalpel has been used on a patient the guard is moved to a disposal position beyond the extended position thus exposing a visual indicia on the handle that indicates that the scalpel should not be reused. The guard also has grooves on the outer surface so as to provide better grip to a surgeon during operation.

18 Claims, 5 Drawing Sheets

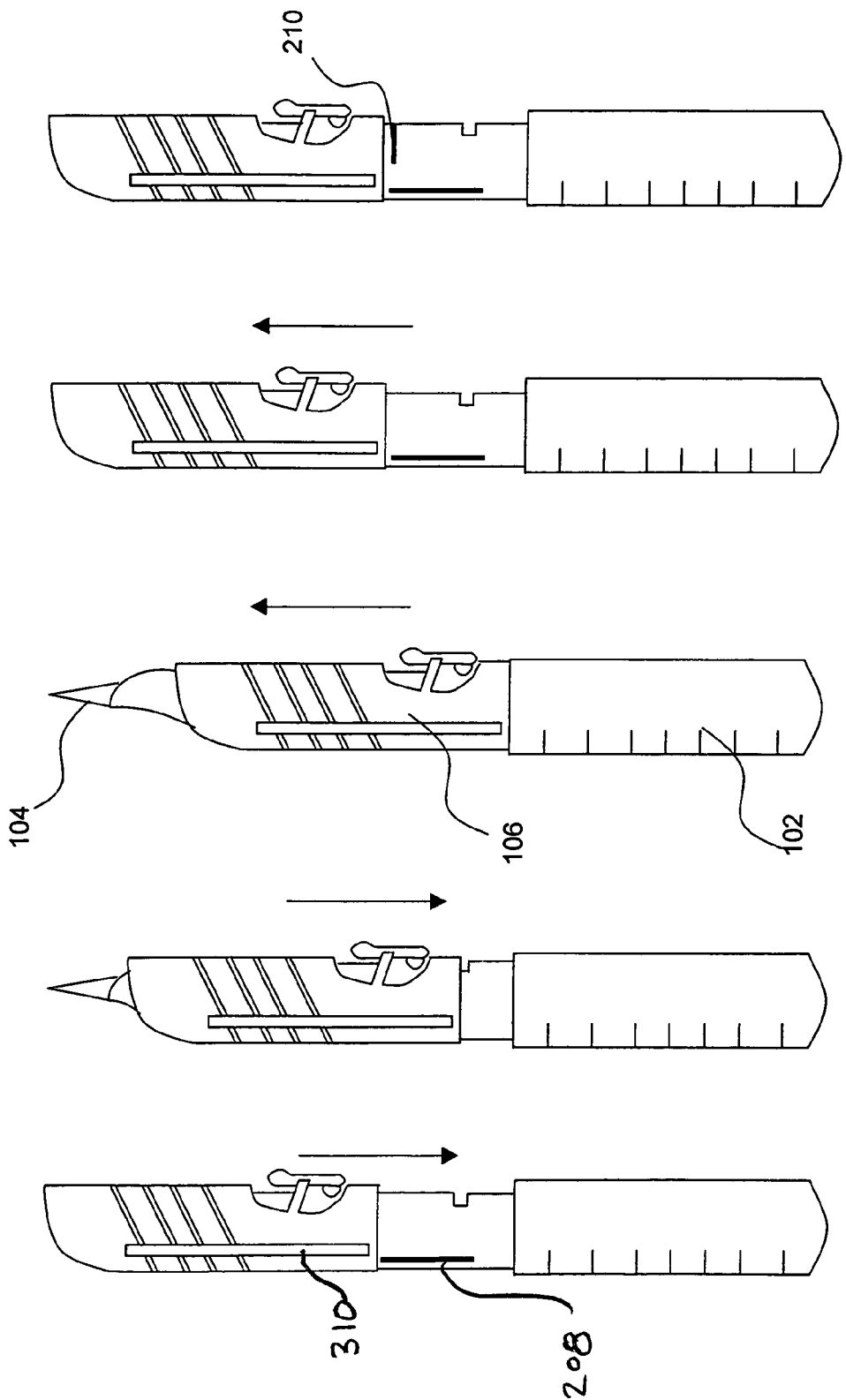

001
DISPOSABLE GUARDED SURGICAL SCALPEL

FIELD OF INVENTION

The present invention relates to the field of surgical incision instruments. In particular, this invention relates to a surgical scalpel with a retractable shield that slides from an initial retracted position to an extended position where it covers the blade and finally to a disposal position.

BACKGROUND

Surgery is an important procedure of modern medicine system. Several incisions and cuts need to be made in the body during the course of a surgery. As surgery involves cutting of body parts, there is very little margin for error during a surgical procedure. Thus it is necessary that the instruments used for surgery have a high degree of accuracy and reliability. There are several surgical instruments that are used for making incisions and cuts during surgery. A scalpel is one such surgical instrument.

A scalpel comprises a handle with a blade attached at one end. It is used by surgeons to make incisions during a surgical procedure. The surgeon holds the scalpel with the handle while making the incisions with the blade. Therefore, the surgeon requires a good grip of the handle to ensure precise incision. Conventional scalpels have handles that do not provide a good grip to the surgeon especially when the surgeon has gloves on his hand.

During a typical surgical procedure several nurses and assistants assist a surgeon by providing him the surgical instruments that the surgeon needs. The transfer of instruments from the assistant to the surgeon should be in an efficient manner as time is a critical factor in surgery. Also, the transfer of a scalpel from the assistant to the surgeon should be such that the surgeon can grip the scalpel without moving his eyes from the surgery. In case the blade of the scalpel is exposed during the transfer of the scalpel, it may result in cuts on the surgeon's hand. Apart from causing pain to the surgeon and breaking his concentration, these seemingly innocuous cuts are very dangerous from the point of view of the surgeon as well as the patient. These cuts may result in the exchange of blood or body fluid between the surgeon and the patients that may lead to transfer of infections from one to the other. The exchange of body fluid may lead to infections as dangerous as Human Immuno Deficiency Virus (HIV) that leads to Acquired Immuno Deficiency Syndrome (AIDS). It may also lead to other fatal infections such as Hepatitis B Virus (HBV). Therefore, there is a lot of danger attached with the use of a scalpel with an exposed blade.

There are some scalpels that have been designed to prevent the occurrence of such "mishaps" and provide a more hygienic operating condition. These scalpel designs have a guard over the blade. The assistant covers the blade with the guard while transferring it to the surgeon. The surgeon removes the guard to expose the blade and then moves the guard to cover the blade again when transferring it back to the assistant.

However, these guarded systems have not been very effective and have a number of drawbacks.

Firstly, many of the guarded scalpels need the use of both hands for moving the guard to cover and uncover the blade. This is not very convenient for the surgeon; the surgeon would prefer to move the guard using just one hand.

Secondly, some of the scalpels allow the blade to be retracted into a slot constructed in the handle. In these scalpels the blade is not fixed; it is moved from the exposed to the retracted position and back. This leads to lesser reliability of the blade as the blade is not fixed and it may move while an incision is being made. This movement of the blade is not desirable during surgery. In an extreme case, the blade may retract during a surgery and may cause irreparable damage.

Third, in most of the scalpels the guard is made of opaque material. Therefore, the blade is not visible when covered by the guard.

The concern for transfer of infections like HIV and HBV during surgery has led to the development of disposable surgical instruments. These instruments are used on just a single patient for one surgery and then disposed off. This ensures better hygiene and protection for the patient and hospital staff during surgery.

There are several existing designs of disposable scalpels. These scalpels are manufactured with "plastic" handles and "metallic" blades unlike conventional scalpels, which are made completely of stainless steel. This makes these disposable scalpels more cost effective.

However, these scalpels have not been able to completely avoid the reuse of the scalpels. There are cases when surgical instruments have been reused by mistake. For example, an operating assistant may, by mistake, use the scalpel (for operating a patient) that has already been used (on another patient). This typically happens in the case when there are no visual indicia to tell that the scalpel has been used before. This greatly increases the risk of transfer of infections.

Another drawback associated with such scalpels is that the guard may sometimes retract at the time of disposal thereby exposing the blade. This may lead to injury to the person handling the disposed scalpels and inadvertently, transfer the existing blood or other contaminated material that is on the disposed scalpels.

Therefore, there is a need for a disposable scalpel that can provide the surgeon with a good grip of the scalpel during surgery. There is also a need for a scalpel with a guard that can prevent any accidental cuts during transfer of the scalpel from the assistant to the surgeon. The guard should be such that the surgeon can conveniently operate it, by using just one hand. The guard should also not retract at the time of disposal of the scalpel. Further, there is a need for visual indicia that tells the assistant or the surgeons that the scalpel has been used and it should be disposed of.

SUMMARY

An object of the present invention is to provide a disposable guarded scalpel that prevents inadvertent cuts during transfer of the scalpel from the assistant to the surgeon and vice versa.

Another object of the present invention is to provide a guard on the scalpel that can be conveniently used by a surgeon to cover or uncover a blade using a single hand.

Yet another object of the present invention is to provide a guard on the scalpel that does not retract during or after the disposal of the scalpel.

Yet another object of the present invention is to provide a scalpel that comprises a blade that is immovably fixed to the scalpel handle.

Yet another object of the present invention is to provide a visual indicia on the scalpel that indicates that the scalpel has been used once and should not be reused.

Yet another object of the present invention is to provide a scalpel that provides a better grip to the surgeon during surgery.

Yet another object of the present invention is to provide a scalpel that can be used comfortably by both left-handed and right-handed users.

The present invention provides a disposable guarded scalpel that comprises a handle, a blade and a guard. The blade is fixed to the end of the handle. The blade is immovable and therefore provides greater confidence to the surgeon for precise incision. The guard can be slid and locked on the handle in three distinct positions: an extended position, a retracted position and a disposal position. In the extended position the guard covers the blade and prevents any inadvertent cuts. The guard is in the extended position during the transfer of the scalpel from the assistants to the surgeon or vice versa. The guard is moved from the extended position to the retracted position to expose the blade for making incisions during surgery. Once the surgery has been performed and the scalpel is to be disposed, the guard can be moved ahead of the extended position to the disposal position. In the disposal position a positive lock, locks the guard and prevents any unintentional movement of the guard. The scalpel of the present invention has provision for a visual indicia to indicate that the scalpel has been used. In the disposal position the visual indicia is exposed on the handle indicating that the scalpel has been used and should not be reused. The guard cannot be unintentionally retracted from this position. Further, the guard has grooves on its upper surface to provide a better grip of the scalpel during surgery.

BRIEF DESCRIPTION OF THE DRAWINGS

The preferred embodiments of the invention will hereinafter be described in conjunction with the appended drawings provided to illustrate and not to limit the invention, wherein like designations denote like elements, and in which:

FIGS. 5a–5e are exemplary drawings illustrating the different positions of the guard of the scalpel in accordance with the preferred embodiment.

DESCRIPTION OF PREFERRED EMBODIMENTS

The present invention provides a disposable guarded surgical scalpel. The scalpel of the present invention includes a handle, a blade fixed to the handle and a guard that is slidably attached to the handle. The guard can be slid and locked on the handle in three distinct positions: a retracted position where the blade is exposed, an extended position where the blade is covered and a disposal position which indicates that the scalpel has been used and should not be reused. In the disposal position a visual indicia on the handle is exposed to indicate that the scalpel should be disposed of. In a preferred embodiment of the present invention the guard has a grooved outer surface to provide a better grip of the scalpel. The handle in the preferred embodiment also has a centimeter scale at one end to aid a surgeon during surgery.

Figure 1:
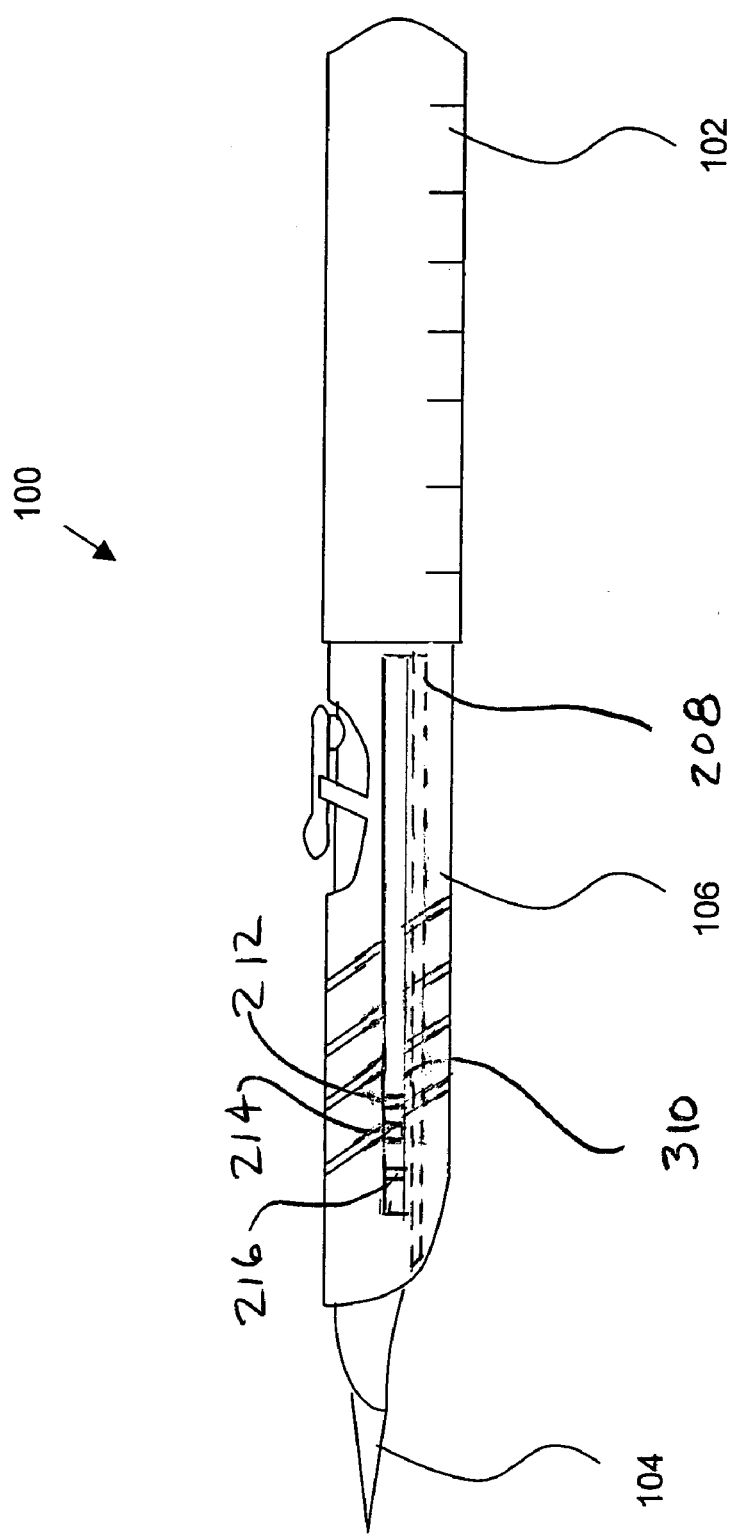
FIG. 1 is an assembled view of a scalpel in accordance with a preferred embodiment of the present invention.

FIG. 1 is an assembled view of a preferred embodiment of the present invention. The disposable guarded surgical scalpel 100 in FIG. 1 includes a handle 102, a blade 104 and a guard 106. Blade 104 is attached to one end of handle 102. Guard 106 is slidably mounted on the same side of handle 102 as blade 104. Guard 106 slides on handle 102 to expose blade 104 at one extreme and covers blade 104 at the other extreme. Further details about handle 102, blade 104 and guard 106 are disclosed in the following paragraphs.

Figure 2A:
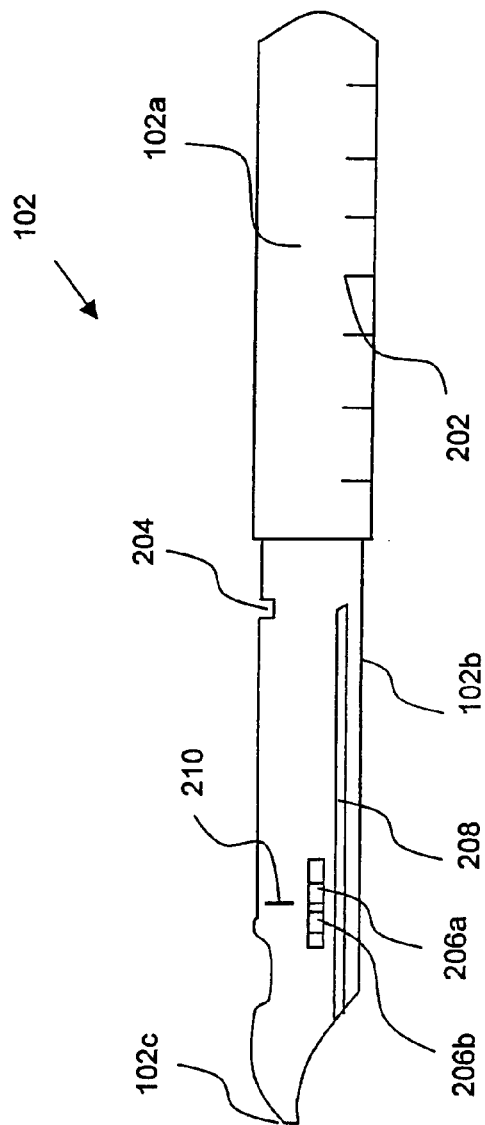
FIG. 2a is a front plan view of a handle of the scalpel, with the blade not attached, in accordance with the preferred embodiment.
Figure 2B:
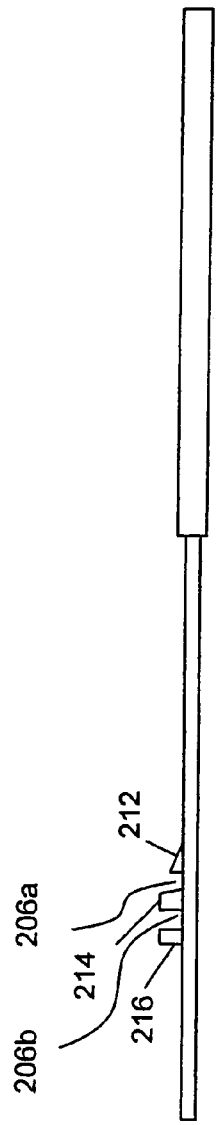
FIG. 2b is a side view from below of the handle of the scalpel in accordance with the preferred embodiment of the current invention.

FIG. 2a is a plan view of handle 102 (without blade 104) used in the preferred embodiment. FIG. 2b is a side view of the handle from below. Handle 102 can be divided into two parts: a proximal part 102a and a distal part 102b. Distal part 102b has a tip 102c at one end. A surgeon holds surgical scalpel 100 at the proximal part 102a while transferring it during a surgery. In a preferred embodiment proximal part 102a of handle 102 has a centimeter scale 202 marked on the surface. Centimeter scale 202 is useful during surgery by providing the surgeon a handy measurement tool. Handle 102 also has a first notch 204 on the edge of distal part 102b. Distal part 102b has an embedded surface feature having a second notch 206a, formed between first and second protuberances 212 and 214 and a third notch 206b, formed between second protuberance 214 and a third protuberance 216, all of which are forward of the notch 204. Third notch 206b is henceforth referred to as positive lock 206b. Distal part 102b further includes a slot 208 on each of its side. Slot 208 extends longitudinally along the distal part 102b of handle 102 below the level of the notches 206a, 206b and defines the sliding displacement of guard 106. Handle 102 further has a visual indicia 210. In a preferred embodiment visual indicia 210 is a painted line or an inscribed groove.

There are several materials that can be used in manufacturing handle 102. In a preferred embodiment the material used is moldable plastic or polymer material such as nylon, ABS etc. These materials are less expensive as compared to material such as stainless steel.

At tip 102c of handle 102 blade 104 is fixed. Blade 104 is rigidly attached to handle 102. Such a rigid attachment of the blade is critical to ensure precision during surgeries. In a preferred embodiment blade 104 is attached to the handle by heat welding. This ensures a tight fit between blade 104 and handle 102.

Blade 104 may be made of metallic materials like stainless steel, carbon steel etc. It would be obvious to one skilled in the art that several other metals and alloys can also be used for manufacturing blade 104.

Figure 3:
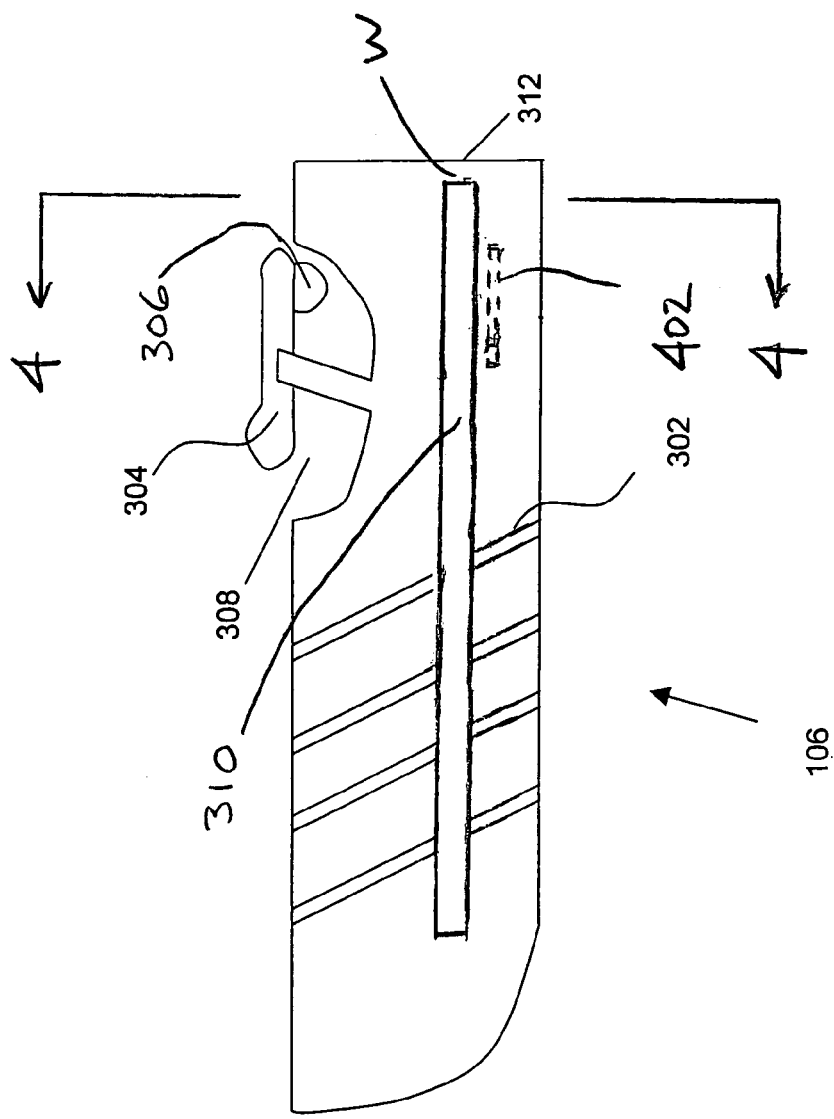
FIG. 3 is a plan view of a guard of the scalpel in accordance with the preferred embodiment.

FIG. 3 is a plan view of guard 106 used in the preferred embodiment. Guard 106 is generally U-shaped at the front opening and is slidably mounted on distal part 102b of handle 102. Guard 106 has a grooved, ribbed or similarly textured outer surface 302. Grooved or ribbed outer surface 302 provides a better grip of the scalpel when in use. Guard 106 also has a biased cantilever lock 304. Cantilever lock 304 has a downward protrusion 306. Protrusion 306 is designed such that it engages in first notch 204 on distal part 102b in the retracted position to prevent any motion when engaged. When guard 106 slides on handle 102 and crosses first notch 204, protrusion 306 on cantilever lock 304 extends through an opening 308 and automatically engages into first notch 204. This prevents any further movement of guard 106. Cantilever lock 304 has to be pressed and guard 106 slid along handle 102 to ensure unlocking. Guard 106 further includes a longitudinal through slot 310 and a rear edge 312, the slot 310 extending parallel to the slots 208 on the handle and slidably receiving the longitudinally aligned protuberances 212, 214, and 216.

Figure 4:
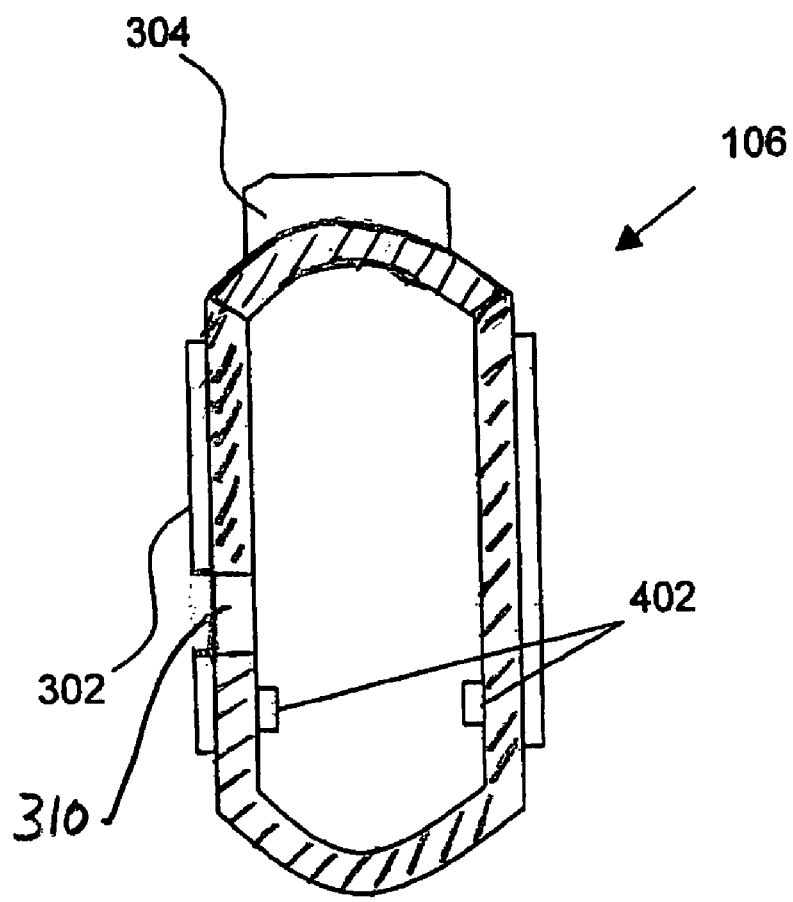
FIG. 4 is a cross-sectional view of the guard of the scalpel along line 4—4 of FIG. 3 in accordance with the preferred embodiment.

FIG. 4 is a cross-sectional view of guard 106. It shows the features on the inner surface of guard 106. There is a pair of longitudinal protrusions 402 on the inner surface of guard 106. Longitudinal protrusions 402 engage into slot 208 (See FIG. 2) in distal part 102b of handle 102. This arrangement constrains the sliding motion of guard 106 over handle 102. The arrangement leaves the least possible clearance between guard 106 and handle 102 so as to ensure minimum lateral movement of guard 106 with respect to handle 102. At the same time the clearance is adequate enough to provide "free" sliding movement. Minimal clearance provides improved precision during surgery while "free" sliding is necessary to ensure comfortable usage.

In a preferred embodiment, guard 106 is made of transparent polymer material such as polycarbonate. Guard 106 and cantilever lock 304 can be molded as a single unit by conventional molding techniques, with cantilever lock 304 biased into engagement with first notch 204 of handle 102 by means of a living hinge formed in the polymer material.

The method of use of the scalpel during surgery is now described with the aid of FIG. 5. The figure shows the different positions of guard 106 during the surgical procedure. FIG. 5a is an exemplary drawing illustrating the extended position of guard 106 in the preferred embodiment. Disposable guarded scalpel 100 would be transferred to a surgeon in this position. In this position blade 104 is completely covered by guard 106. FIG. 5b is an exemplary drawing illustrating an intermediate position as guard 106 is moved along slot 208 from the extended position to the retracted position. FIG. 5c is an exemplary drawing illustrating the retracted position of guard 106. In this position the blade is completely exposed for making incisions. FIG. 5d is an exemplary drawing illustrating the extended position of guard 106. FIG. 5e is an exemplary drawing illustrating the disposal position of guard 106. In this position the scalpel is disposed of after the completion of the surgery.

The guarded scalpel of the present invention is initially in the extended position as shown in FIG. 5a where guard 106 covers blade 104 completely. In this position the web portion W of guard 106 between slot 310 and rear edge 312 is engaged into second notch 206a thus limiting the motion of guard 106 with respect to handle 102. This prevents any unintentional exposure of blade 104. The surgical scalpel is supplied to users in the extended state. In the course of a surgery, an assistant would transfer the scalpel to the surgeon in the extended position. The surgeon can single handedly slide guard 106 backwards so as to disengage slot 310 and second notch 206a as the sloping walls of first protuberance 212 permit easy two-way (back and forth) motion. The surgeon can then slide guard 106 to the retracted position as shown in FIG. 5c. Thus, guard 106 moves from extended position of FIG. 5a to retracted position of FIG. 5c through intermediate position of FIG. 5b. In the retracted position, protrusion 306 of cantilever lock 304 engages into first notch 204 and prevents any forward or backward movement of guard 106. In this position, guard 106 covers distal part 102b of handle 102. The surgeon holds grooved surface 302 of guard 106 during incision.

After making one or more incisions the surgeon may press cantilever lock 304 and advance guard to the extended position where slot 310 of guard 106 again engages into second notch 206a. The surgeon would then pass the scalpel back to the assistant. The surgeon may use the scalpel several times in the course of a surgery. When the surgery is over the surgeon or the assistant would advance guard beyond the extended position to the disposal position as shown in FIG. 5e. In this position the portion of guard 106 between slot 310 and rear edge 312 is engaged in positive lock 206b and it becomes very difficult to disengage the positive lock 206b and retract guard 106 because of the substantially vertical walls formed by protuberances 214 and 216 which form lock 206b. It is more difficult to disengage slot 310 and positive lock 206b (in the disposal position) as compared to slot 310 and notch 206a (in the extended position). In the disposal position, visual indicia 210 on handle 102 is exposed and indicates that the scalpel has been used and should not be reused.

Advantages

The disposable guarded scalpel of the present invention has several advantages over existing surgical scalpels.

Firstly, the scalpel provided by the present invention provides more reliability compared to other existing scalpels. This is because the blade is rigidly fixed to the handle thus preventing any undesirable movement of the blade during surgery. Also, the low clearance between the guard and the handle prevents any undesirable movement between the guard and the handle.

Secondly, the scalpel provided by the present invention can be conveniently used by a surgeon using a single hand and without having to look at the scalpel. This ensures increased concentration of the surgeon during surgery. The surgeon is also aided by the grooved outer surface of the guard. It provides a better grip of the scalpel during surgery.

Third, the scalpel provided by the present invention provides a visual indicia that clearly indicates that the scalpel has been used and should not be reused. This prevents any unintentional reuse of an already used scalpel ensuring greater protection for the patients.

Fourth, the scalpel provided by the present invention provides an enhanced locking system to ensure safety when the scalpel is disposed off. The enhanced locking system ensures that the guard does not retract when the scalpel is disposed.

Fifth, the use of transparent guard in the scalpel makes the blade visible to the surgeon in the extended position. This helps the surgeon to choose a scalpel based on the requirement of a surgery.

Sixth, the design of the scalpel provided by the present invention allows the scalpel to be used comfortably by both right-handed users and left-handed users.

While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the invention as described in the claims.

What is claimed is:

1. A disposable guarded surgical scalpel comprising:
   a. an elongated handle having front and rear ends and left and right sides, a first external notch between the ends and a series of longitudinally aligned external protrusions on one side, forward of said first notch, forming second and third notches;
   b. a blade fixed to the front of the handle;
   c. a guard having left and right flat sides, slidably mounted over a portion of the left and right sides of the handle, the guard being movable longitudinally back and forth between a first, retracted position where the blade is exposed and a second, extended position where the blade is covered, the guard also being movable to a third, disposal position covering said blade beyond the extended position, and wherein the guard is lockable in all the three positions, the guard having a longitudinal through slot on a side of the guard over the side of the handle having the external series of protrusions, and a rear edge, wherein the flat side portion of the guard between the slot and the rear edge engages with the series of protrusions of the handle to selectively lock the guard with respect to the handle in said second and third positions; and d. a lock, disposed at an outer surface of the guard and being externally accessible by a user, wherein the lock retains the guard in the retracted position by engagement with the first notch, and wherein the guard is capable of being unlocked from the retracted position by the user pressing the lock longitudinally forward to displace the lock relative to the guard and the handle.

2. The disposable guarded surgical scalpel of claim 1 wherein the handle comprises a slot on each side below the series of protrusions, and wherein the guard further comprises a longitudinal protrusion on each side of its inner surface below the through slot, that engages in a slot of the handle to constrain the sliding motion of the guard over the handle.

3. The disposable guarded surgical scalpel of claim 1 wherein the first notch is disposed along an upper edge of the handle, the lock at the outer surface of the guard includes a downwardly disposed protrusion, the downwardly disposed protrusion engaging the first notch of the handle to lock the guard in the retracted position.

4. The disposable guarded surgical scalpel of claim 1 wherein the protrusions of the handle define a second notch and wherein the portion of the guard between the slot and the rear edge engages in the second notch to lock the guard in the extended position.

5. The disposable guarded surgical scalpel of claim 4 wherein the engagement in the third position locks the guard permanently.

6. The disposable guarded surgical scalpel of claim 1 wherein the protrusions of the handle define a third notch forming a positive lock and wherein the portion of the guard between the slot and the rear edge engages in the positive lock to permanently lock the guard in the disposal position.

7. The disposable guarded surgical scalpel of claim 1 wherein the guard is transparent.

8. The disposable guarded surgical scalpel of claim 1 wherein the outer surface of the guard is textured to provide better grip of the scalpel.

9. The disposable guarded surgical scalpel of claim 1 wherein the handle further includes a visual indicia that is exposed behind the rear edge of the guard only in the disposal position.

10. The disposable guarded surgical scalpel of claim 1 further comprising:
a. a pair of slots, each slot in the pair of slots being located on one side of the handle; and
b. a pair of longitudinal protrusions, each longitudinal protrusion in the pair of longitudinal protrusions being located on one side of the guard, wherein the pair of longitudinal protrusions slide into the pair of slots in the handle.

11. The disposable guarded surgical scalpel of claim 1 wherein the lock at the outer surface of the guide projects outwardly from the guard and the lock and the guard are molded as a single unit.

12. The disposable guarded surgical scalpel of claim 1 wherein the lock at the guard is molded as a single unit with the guard, and is biased into engagement with the first notch of the handle by an integral living hinge.

13. A disposable guarded surgical scalpel comprising:
a. a substantially flat handle having top and bottom edges and two sides, with a longitudinal slot on each side adjacent the bottom edge, the handle further having a first notch on the top edge of the handle and a first protuberance, a second protuberance, and a third protuberance extending from a side of the handle forward of the first notch and above one of said slots, wherein the first protuberance and the second protuberance forms a second notch and the second protuberance and the third protuberance forms a third notch;
b. a blade fixed to the handle;
c. a guard slidably mounted on the handle having a longitudinal protrusion on each side of the inner surface that slides in the slot on each side of the handle as the guard moves between a first retracted position where the blade is exposed and a second extended position where the blade is covered, the guard also being movable to a third disposal position covering the blade beyond the extended position, the guard having a through slot parallel to a slot in the handle, in which said protuberances are received and a rear edge, wherein upon forward sliding of the guard the portion of the guard between the slot and the rear edge engages in the second notch to lock the guard with respect to the handle in the second extended position and upon further forward sliding the portion of the guide between the slot and the rear edge engages in the third notch to lock the guard with respect to the handle in the third disposal position; and
d. a cantilever lock, the cantilever lock disposed at an outer surface of the guard and being externally accessible by a user, wherein the cantilever lock locks the guard in the first retracted position, and wherein the guard is unlocked from the first retracted position to permit forward sliding, by pressing the cantilever lock.

14. The disposable guarded surgical scalpel of claim 13 wherein the guard is transparent.

15. The disposable guarded surgical scalpel of claim 13 wherein the outer surface of the guard is grooved to provide better grip of the scalpel.

16. The disposable guarded surgical scalpel of claim 13 wherein the handle further includes a visual indicia that is exposed behind the rear edge of the guard only in the disposal position.

17. The disposable guarded surgical scalpel of claim 16 wherein the visual indicia on the handle is a distinctly colored line.

18. The disposable guarded surgical scalpel of claim 13 wherein the cantilever lock is molded as a single unit with the guard, and is biased into engagement with the first notch of the handle by an integral living hinge.

* * * * *